US011478221B2

(12) United States Patent
van Rens (10) Patent No.: US 11,478,221 B2
(45) Date of Patent: Oct. 25, 2022

(54) ULTRASOUND IMAGING SYSTEM USING AN ARRAY OF TRANSDUCER ELEMENTS AND AN IMAGING METHOD

(71) Applicant: KONINKLIJKE PHILIPS N.V., Eindhoven (NL)

(72) Inventor: Antonia Cornelia van Rens, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/968,987

(22) PCT Filed: Feb. 14, 2019

(86) PCT No.: PCT/EP2019/053657
§ 371 (c)(1),
(2) Date: Aug. 11, 2020

(87) PCT Pub. No.: WO2019/158640
PCT Pub. Date: Aug. 22, 2019

(65) Prior Publication Data
US 2021/0052248 A1    Feb. 25, 2021

(30) Foreign Application Priority Data
Feb. 15, 2018   (EP) .................................... 18156934

(51) Int. Cl.
*A61B 8/06*    (2006.01)
*A61B 8/12*    (2006.01)
(Continued)

(52) U.S. Cl.
CPC .............. *A61B 8/4488* (2013.01); *A61B 8/06* (2013.01); *A61B 8/0883* (2013.01); *A61B 8/12* (2013.01);
(Continued)

(58) Field of Classification Search
CPC ....... A61B 8/4488; A61B 8/06; A61B 8/0883; A61B 8/12; A61B 8/4494; A61B 8/5207;
(Continued)

(56) References Cited

U.S. PATENT DOCUMENTS 4,159,462 A * 6/1979 Rocha ................. G01S 15/8927
367/87
4,167,753 A * 9/1979 Lynk .................... G01S 7/52044
367/105
(Continued)

FOREIGN PATENT DOCUMENTS

EP   1762182 A1   3/2007
JP   H09154844 A   6/1997
(Continued)

OTHER PUBLICATIONS

International Search Report and Written Opinion for International Application No. PCT/EP2019/053657, filed Feb. 14, 2019, 14 pages.
(Continued)

*Primary Examiner* — Colin T. Sakamoto (57) ABSTRACT

An ultrasound (US) system is discloses and includes a plurality of transducer elements forming a one-dimensional array and a plurality of bias voltage circuits. Each bias voltage circuit is in communication with a respective first set of the transducer elements and configured to apply a bias voltage to its respective first set of the transducer elements. The US system also included a second plurality of transmit and receive circuits. Each transmit and receive circuit is in communication with a respective second set of transducer elements and configured to stimulate signal transmission or reception of the respective second set of transducer elements.

20 Claims, 3 Drawing Sheets

(51) Int. Cl.
*A61B 8/00* (2006.01)
*A61B 8/08* (2006.01)

(52) U.S. Cl.
CPC .......... *A61B 8/4494* (2013.01); *A61B 8/5207* (2013.01); *A61B 8/5246* (2013.01)

(58) Field of Classification Search
CPC ....... A61B 8/5246; A61B 8/54; A61B 8/0891; A61B 8/445; A61B 8/4461
See application file for complete search history.

(56) References Cited

U.S. PATENT DOCUMENTS

| | | | |
|---|---|---|---|
| 5,617,862 A * | 4/1997 | Cole | G01S 15/8913 600/459 |
| 6,499,348 B1 * | 12/2002 | Mamayek | B06B 1/0292 367/153 |
| 9,310,485 B2 | 4/2016 | Degertekin et al. | |
| 2007/0194658 A1 * | 8/2007 | Zhang | A61B 17/1325 310/314 |
| 2008/0027310 A1 * | 1/2008 | Tamaroff | A61B 5/055 606/1 |
| 2008/0089181 A1 | 4/2008 | Adachi et al. | |
| 2010/0256501 A1 | 10/2010 | Degertekin | |
| 2014/0187960 A1 * | 7/2014 | Corl | A61B 8/4483 600/466 |
| 2014/0288428 A1 | 9/2014 | Rothberg et al. | |
| 2015/0087991 A1 * | 3/2015 | Chen | G01S 7/52025 330/253 |

FOREIGN PATENT DOCUMENTS

| | | | |
|---|---|---|---|
| WO | 2015086413 A1 | 6/2015 | |
| WO | WO-2016091985 A1 * | 6/2016 | .......... B06B 1/0292 |
| WO | 2016139065 A1 | 9/2016 | |

OTHER PUBLICATIONS

Satir, et al., "An Annular CMUT Array Beamforming System for High-Frequency Side Looking IVUS Imaging", IEEE Ultrasonics Symposium Proceedings, pp. 563-566.

* cited by examiner

ULTRASOUND IMAGING SYSTEM USING AN ARRAY OF TRANSDUCER ELEMENTS AND AN IMAGING METHOD

RELATED APPLICATIONS

This application is the U.S. National Phase application under 35 U.S.C. § 371 of International Application No. PCT/EP2019/053657, filed on Feb. 14, 2019, which claims the benefit of and priority of European Application No. 18156934.4, filed Feb. 15, 2018. These applications are incorporated by reference herein.

FIELD OF THE INVENTION

This invention relates to an ultrasound imaging system using an array of transducer elements, in particular capacitive micromachined ultrasound transducer (CMUT) elements.

BACKGROUND OF THE INVENTION

An array of transducer elements may be used when imaging is desired in a confined space.

One key example is for intravascular ultrasound (IVUS) imaging. This is widely used in interventional cardiology as a diagnostic tool for a diseased vessel, such as an artery, within the human body to determine the need for treatment, to guide an intervention, and/or to assess its effectiveness. To perform an IVUS imaging study, an IVUS catheter that incorporates one or more ultrasound transducers is passed into the vessel and guided to the area to be imaged.

The transducers emit and receive ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by a transducer and passed to an IVUS imaging system, which is connected to the IVUS catheter by way of a patient interface module (PIM). The imaging system processes the received ultrasound signals to produce a cross-sectional image of the vessel where the device is placed.

There are two types of IVUS catheters commonly in use today: rotational and solid-state. For a typical rotational IVUS catheter, one or more ultrasound transducer elements are located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS catheters carry an ultrasound scanner assembly that includes an array of ultrasound transducers, such as a one-dimensional array, distributed around the circumference of the device and connected to a set of transducer control circuits. The array and its corresponding circuitry are often referred to as the imaging core or scanner of the catheter. Often one dimensional array may be described as a "linear array" having a 1×N array of elements in terms of the logical configuration of components. The term "one dimensional" or "linear" do not imply that the actual physical transducer elements are arranged along a physically straight line.

For traditional image generation, transducer control circuits may select individual transducers of the array for transmitting an ultrasound pulse and for receiving the echo signal. By stepping through a sequence of transmitter-receiver pairs, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with cabling and connector to a patient interface module or to a computing system.

A limiting factor of solid-state arrays is that an increased number of transducers is required to achieve high frequency images. Additionally, separate circuits are also required for each transducer element to carry out send/receive functions to the transducer element. For example, a capactive micromachined ultrasonic transducer (cMUT) catheter of 1 mm may include about 100 cMUT transducer elements (each including multiple drums connected in parallel) placed along the circumference of the catheter, and each of those transducer elements requires its own transmit/receive circuit.

Due to the increased number of transducer elements and their corresponding transmit/receive circuitry, high frequency IVUS is inherent with increased length and diameter of the imaging core, which is synonymous with increased catheter diameter and reduced flexibility of the distal portion of the catheter that houses the imaging core. As a result, traditional IVUS catheters must limit their frequency to maintain a practical size for traversing tortuous lumens of the body, such as the vasculature.

WO 2016/139065 discloses a CMUT ultrasound system in which a series of temporally distinct pulses are generated so that an effective broadband pulse echo is generated from a series of narrowband pulses.

US 2008/089181 discloses an ultrasonic transducer cell having a particular configuration for reducing a DC bias voltage or eliminating the need for a DC bias voltage.

SUMMARY OF THE INVENTION

According to examples in accordance with an aspect of the invention, there is provided an ultrasound system, comprising:

a plurality of transducer elements forming a one-dimensional array;

a first plurality of bias voltage circuits, each bias voltage circuit being in communication with a respective first set of the transducer elements and configured to apply a bias voltage to its respective first set of the transducer elements;

a second plurality of transmit and receive circuits, each transmit and receive circuit being in communication with a respective second set of transducer elements and configured to stimulate signal transmission or reception of the transducer elements of its respective second set;

wherein the transducer elements of at least one first set differ from the transducer elements of at least one second set such that only a portion of transducer elements of the second set are arranged to be activated by its respective transmit and receive circuit upon application of a bias voltage to the at least one first set of the transducer elements by the respective bias voltage circuit.

The present invention relates to systems and methods that enable high frequency intraluminal imaging, such as IVUS or intra-cardiac echography (ICE), by reducing an amount of circuitry and wiring required to control the functions of one or more transducer array elements of an intraluminal device (e.g. catheter, guidewire, probe, etc.). In particular, aspects of the invention provide for selectively grouping transducers of an array that receive bias voltages from bias voltage circuitry and that are controlled by transmit and receive circuitry (also referred to as pulser/receiver circuitry). The selective grouping of the invention allows the same transmit and receive circuitry to stimulate one or more transducer elements to transmit signals while stimulating one or more other transducer elements to receive signals. Since a single transmit/receive circuit can, in accordance with the invention, drive transmit/receive functions of multiple transducer elements, less wiring is required to interconnect the transducer and the overall the size of imaging core can be reduced. As a result, systems and methods of the invention enable higher frequency imaging while maintaining a smaller device footprint capable of, e.g., traversing the lumens of the vasculature.

There is provided an ultrasound system (imaging core), comprising:

a plurality of transducer elements;

a first plurality of circuits comprising bias voltage circuits; and a second plurality of circuits comprising transmit and receive circuits, wherein each transducer element is adapted to be activated for transmission or reception by the application of a bias voltage and control by a transmit and receive circuit, wherein each bias voltage circuit is connected to a respective first set of transducer elements, wherein each transmit and receive circuit is connected to a respective second set of transducer elements, wherein each first set comprises a plurality of transducer elements, each one from a different second set, and wherein each second set comprises at most one transducer element from any first set.

The full plurality of transducer elements is divided into two collections of sets which overlap in a grid-type or matrix-type manner. It is noted that the first set do not overlap with each other and the second set do not overlap with each other. At the overlaps between the sets of the two types, a transducer element can be operated to transmit or receive, because the bias voltage can be applied by the bias voltage circuit of the associated first set and the transmit and receive circuit of the associated second set can be operated to perform a transmit or receive function. This arrangement makes use of the need for two separate drive signals to be applied to the transducer element in order for the transmit or receive function to be effective.

The invention is of particular interest for a phased array approach (i.e. a synthetic aperture approach) in which one transducer element is used for transmit and one or more surrounding elements are used for receive, in a sequence. The eventual image is built up by data processing after the image acquisition process is completed.

A single transducer element may be operated to transmit because one element from any first set may be selected. However, multiple elements could if desired be stimulated to transmit. Similarly, a single transducer element may be operated to receive. Again, multiple elements could if desired be stimulated to receive.

This arrangement reduces the number of bias circuits and transmit and receive circuits, and also the amount of wiring (cabling) needed. In certain embodiments, when one transducer element in a second set is operating in transmit mode, the other transducer elements in that second set are not available for use in receive mode. By spacing the different transducer elements of each second set apart, this does not detract from the imaging capability in that a signal can be transmitted and received at the location where the echo will carry the most information.

For clarity, it is noted that all first sets of the transducer elements together include all transducer elements of the array and all second sets together include all transducer element of the array.

Each second set preferably comprises a second plurality of transducer elements, each from a different first set.

As a minimum, each second set may be a single transducer element, so that sharing only takes place of the bias voltage circuits. However, there is preferably also sharing of both bias voltage circuits and transmit and receive circuits.

Each first set may further comprises a group of neighboring transducer elements.

By activating a group using the bias voltage circuit, one or more transducer elements in the group may be used for transmit and one or more may be used for receive. However, other transducer elements, in other groups, may also or instead be used for receive.

Each second set may comprise a cluster of non-neighboring transducer elements. Each second set for example comprises a plurality of non-neighboring transducer elements spaced uniformly along the array.

This spacing means that transducer elements which cannot be operated at the same time (to perform different functions) are spaced apart along the array. The combination of sets based on neighboring groups of transducer elements and sets based on spaced transducer elements enables the grid-type functionality mentioned above to be achieved.

Each transducer element for example comprises a plurality of transducer cells.

These cells are preferably connected in parallel, so that they are controlled by shared control lines. Each transducer cell for example comprises a CMUT cell. These devices require both a DC bias and transmit and receive control to be made operational. The DC bias is for example used to operate the cell in a collapsed mode.

The plurality of transducer elements may form an array, which might comprise an annulus with each transducer element facing radially outwardly. This is particularly suitable for imaging within a conduit, such as a blood vessel.

The system for example comprises a number $N_1$ of transducer elements in each first set, a number M of second sets and an aperture P.

In this case, the arrangement may satisfy:

$$P=M-N_1+1$$

The aperture size, P, reflects the range of elements that are fired and sensed to form the image at one particular location. Image formation is done retrospectively. However, per firing, this range of elements that are combined can be smaller. Recent innovations in beamforming have shown that it can be interesting to use closely spaced transmit and receive elements to form a sub-aperture, and to shift such a sub-aperture along the catheter. For example, if the aperture size is 20 (element numbers 1 . . . 20) then the first sub-aperture could use elements [1 . . . 5], the second sub-aperture could use elements [2 ... 6] and so up to the sixteenth aperture which uses elements [16 ... 20] ... The retrospective beamforming will then combine all results in order to build the full aperture.

The maximum sub-aperture size (i.e. which can always be achieved) is of interest and this is expressed by the value P.

By way of example, the total number of transducer elements is in the range 20 to 200. There may be 3 to 10 elements in each first set, and there may be 2 to 5 elements in each second set.

The invention also provides an intravascular ultrasound device, comprising:

a catheter body; and an ultrasound imaging system as defined above coupled to a distal portion of the catheter body.

This defines one beneficial application of the imaging system of the invention,

The invention also provides a ultrasound imaging method for performing imaging using an array of transducer elements forming a one-dimensional array, with a first plurality of bias voltage circuits; and a second plurality of transmit and receive circuits, wherein each transducer element is adapted to be activated for transmission or reception by the application of a bias voltage and connection to a transmit and receive circuit, wherein the method comprises:

operating a bias voltage circuit thereby to provide a bias voltage to a respective first set of transducer elements;

operating a first transmit and receive circuit thereby to provide a transmit function to a first respective second set of transducer elements; and operating a second transmit and receive circuit thereby to provide a receive function to a second respective second set of transducer elements, wherein the first set comprises a plurality of transducer elements, each one from a different second set, and wherein each second set comprises a portion of transducer elements from any first set.

In another embodiment, each second set comprises at most one transducer from any first set.

This method provides one (second) set in transmit mode, and another (second) set in receive mode. However, only the transducer elements connected to a bias voltage are active. This method allows a single transducer element to be in transmit mode and a single transducer element to be in receive mode.

The first set may comprise a group of neighboring transducer elements and the second sets each comprise a cluster of non-neighboring transducer elements.

By activating a group using the bias voltage circuit, one or more transducer elements in the group may be used for transmit and one or more may be used for receive. However, other transducer elements, in other groups, may also or instead be used for receive.

The method may comprise, for each transducer element, providing the bias voltage, the transmit function and the receive function to a set of transducer cells.

The method may comprise performing imaging using an annulus of radially outwardly facing transducer elements.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound imaging system, comprising an array of transducer elements. A first plurality of bias voltage circuits and a second plurality of transmit and receive circuits are provided, but they are used in a shared manner. To enable this, each bias voltage circuit is connected to a respective first set (e.g. neighboring group) of transducer elements and each transmit and receive circuit is connected to a respective second set (e.g. spaced apart cluster) of transducer elements. Each first set comprises a plurality of transducer elements, each one from a different second set, and each second set comprises a portion, of transducer elements (in a specific embodiment at most one transducer element) from any first set. This arrangement makes use of the need for two separate drive signals to be applied to the transducer element in order for the transmit or receive function to be effective.

Figure 1:
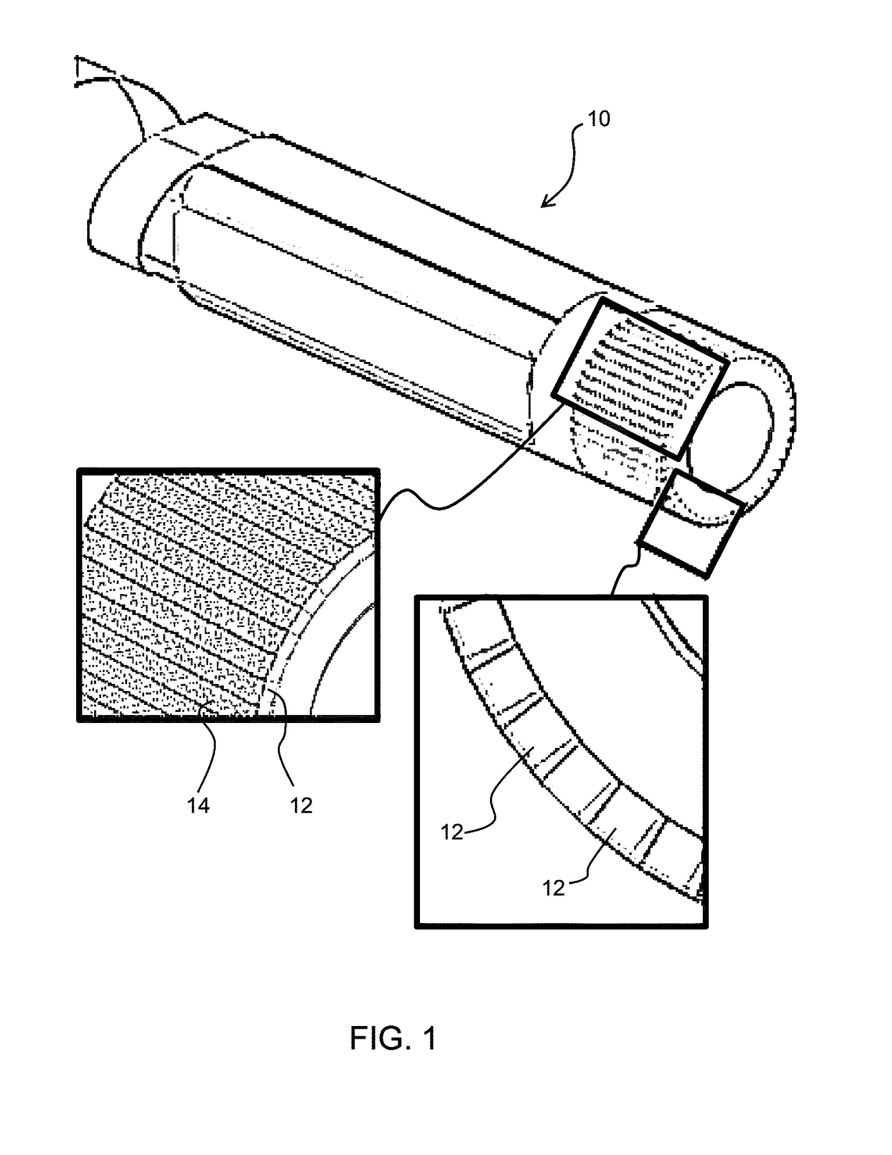
FIG. 1 shows the type of ultrasound imaging system to which the invention is particularly applicable.

FIG. 1 shows the type of ultrasound imaging system to which the invention is particularly applicable.

FIG. 1 shows an intravascular ultrasound system 10 in the form of a probe for positioning at the end of catheter body. The system 10 comprises a 1 dimensional array of transducer elements 12 at the distal tip of the probe. ASICs are mounted further back behind the tip. By 1 dimensional is meant the transducer elements are in a single line rather than a 2D grid. The line in this example is a circle, hence it is clear that 1 dimensional does not imply a straight physical line, but instead refers to the type of array layout more generally.

Each transducer element 12 may include one or more transducer cells or drums 14. The transducer cells 14 may be arranged in along the transducer element in a line configuration, although other configurations are possible. In certain embodiments, the transducer elements are capacitive micromachined ultrasound transducer (CMUT). CMUTs are ultrasound transducer elements which can be batch manufactured by semiconductor processes, for example using the same processes used to produce the ASIC circuitry needed by the ultrasound probe, such as a CMOS process. CMUT transducer cells are tiny diaphragm-like devices with electrodes that convert the sound vibration of a received ultrasound signal into a modulated capacitance.

For transmission, the capacitive charge applied to the electrodes is modulated to vibrate/move the diaphragm of the cells and thereby transmit an ultrasound wave. Since these diaphragms are manufactured by semiconductor processes the devices generally can have dimensions in the 10-500 micrometer range, with the diaphragm diameter for instance being selected to match the diaphragm diameter to the desired resonance frequency (range) of the diaphragm, with spacing between the individual diaphragms less than a few micrometers. Many such individual CMUT cells can be connected together and operated in unison as a single transducer element. For example, from four up to tens (e.g. 50) of CMUT cells can be coupled together to function in unison as a single transducer element.

The manufacture of CMUT transducer-based ultrasound systems is therefore more cost-effective compared to PZT-based systems. Moreover, due to the materials used in such semiconductor processes, the CMUT transducers exhibit much improved acoustic impedance matching to water and biological tissue, which obviates the need for (multiple) matching layers and yields an improved effective bandwidth.

In order to optimize the acoustic power (output pressure) produced by the CMUT cells, the CMUT cells may be operated in so-called collapse mode in which the CMUT cells of a transducer element are driven by a bias voltage that drives a central part of the diaphragm or flexible membrane across the gap onto the opposing substrate and provided with a stimulus having a set frequency that causes the diaphragm or flexible membrane to resonate at the set frequency. The voltage at which the membrane goes into collapse is called the collapse voltage, $V_C$. The structure of a typical CMUT cell is discussed further below.

Thus, the operation of a CMUT cell may require the combination of a bias voltage as well as a pulse transmit signal or a pulse receive function. This requirement for two separate signal connections gives the opportunity to provide a matrix type addressing scheme, whereby only transducer cells at the intersections are activated.

The invention is based on providing a first set of bias voltage circuits and a second set of transmit and receive circuits. There are fewer bias voltage circuits than transducer elements and preferably also fewer transmit and receive circuits than transducer elements. This reduces the amount of wiring and the amount of circuitry. The multiple transducer elements connected to one bias circuit are operated in parallel and the multiple transducer elements connected to one transmit and receive circuit are also operated in parallel.

Each bias voltage circuit is connected to a respective first set of transducer elements.

Figure 2:
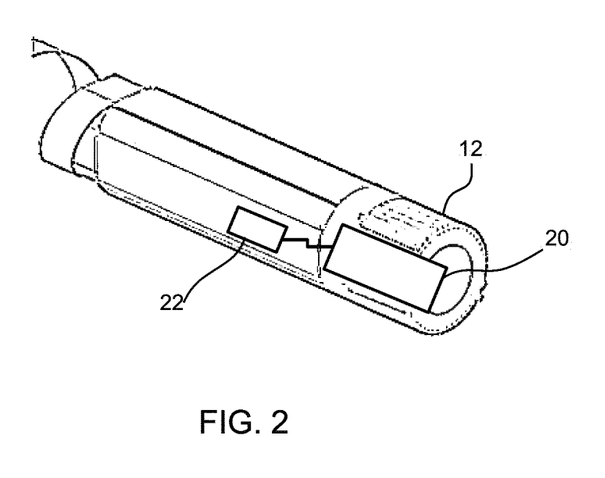
FIG. 2 shows how each bias voltage circuit is connected to a respective first set of transducer elements.

This is shown in FIG. 2, wherein a first set 20 of transducer elements 12 connects to a shared bias voltage circuit 22. There is one such bias voltage circuit 22 for each first set.

Each transmit and receive circuit is connected to a respective second set of transducer elements.

Figure 3:
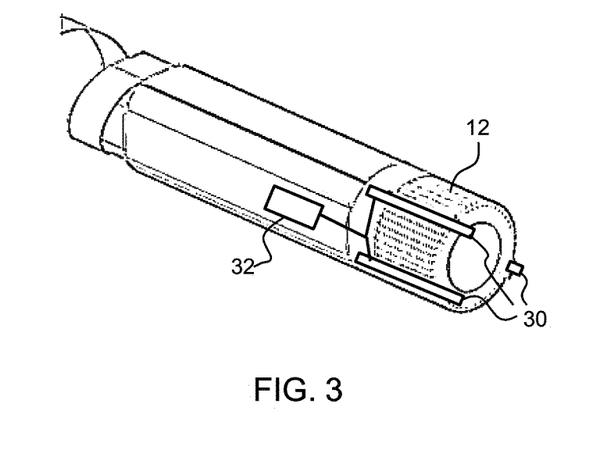
FIG. 3 shows how each transmit and receive circuit is connected to a respective second set of transducer elements.

This is shown in FIG. 3, wherein a second set 30 of transducer elements 12 connects to a shared transmit and receive circuit 32. There is one such transmit and receive circuit 32 for each second set.

The rectangles 20, 30 simply illustrate the locations of the transducer elements which are grouped to form a set.

The bias voltage circuits 22 and transmit/receive circuits 32 are communicatively coupled to the one or more transducer elements via electrical connections. The electrical connections may be wiring and/or printed connections. In certain embodiments, the circuitry 22, 32 may be positioned proximal to the transducer elements, distal to the transducer elements, concentric with the transducer elements (e.g. in parallel), and/or combinations thereof. The bias voltage circuits 22 and transmit/receive circuits 32 may be incorporated into one or more application-specific integrated circuits (ASICs).

The present invention not only allows reducing circuitry complexity of the ultrasound system, but it also reduces amount of interconnects (cabling) required to operate such as a system. Further, present invention allows reducing amount of conductive couplings in between the circuitries and the ultrasound elements thereby further permitting to maintain a smaller device footprint capable of, e.g., traversing the lumens of the vasculature.

Preferably, the first sets 20 and the second sets 30 cover, in some fashion, the same transducers. For example, the first sets 20 together may include all transducer elements of the array and all of the second sets 30 together include all transducer element of the array. Although there may be circumstances when an array includes one or more transducer elements of the array are not included either the first sets 20 or the second sets 30. Furthermore, each first set 20 comprises a plurality of transducer elements, each one from a different second set, and each second set 30 comprises an element from any first set. In a specific embodiment each first set 20 comprises a plurality of transducer elements, each one from a different second set, and each second set 30 comprises at most one transducer element from any first set.

In certain aspects, the full set of transducer elements is divided into two collections of sets which overlap in a grid-type manner. At the overlaps between the sets a transducer element can be operated to transmit or receive by applying a bias voltage using the bias voltage circuit 22 of the associated first set 20 (of which the transducer element is a member) and the transmit and receive circuit 32 of the associated second set 30 (of which the transducer element is a member).

In a particular example, the first sets 20 each comprise a group (G) of neighboring elements and the second sets each comprise a cluster (C) of "x" transducer elements located at an angle of 360/x degrees. Thus, the transducer elements of each second set (cluster) are distributed evenly around the array.

By controlling the bias voltages and stimulating the transmit and receive circuits (i.e. a pulser circuit) selectively, it is possible to stimulate any individual transducer element for transmit (TX) and a selected number (one or more) transducer elements for receive (RX) while sharing the transmit and receive hardware.

This approach is particularly suited for sideward looking circular transducer arrays such as in IVUS, as unwanted ultrasonic energy generated by non-selected elements completely disappears from the imaging area. This is important as it is hard to turn off a CMUT cell completely in transmit mode even when the desired bias voltage is not applied. This is due to the non-linear behavior of the CMUT cell in combination with the strong transmit pulses.

The operation of the system will be better understood from the example table below.

TABLE 1

|  | G1 | G2 | G3 | G4 | G5 | G6 |
|---|---|---|---|---|---|---|
| C1 | 1 |  |  | 16 |  |  |
| C2 | 2 |  |  | 17 |  |  |
| C3 | 3 |  |  | 18 |  |  |

TABLE 1-continued

|  | G1 | G2 | G3 | G4 | G5 | G6 |
|---|---|---|---|---|---|---|
| C4 | 4 |  |  | 19 |  |  |
| C5 | 5 |  |  | 20 |  |  |
| C6 |  | 6 |  |  | 21 |  |
| C7 |  | 7 |  |  | 22 |  |
| C8 |  | 8 |  |  | 23 |  |
| C9 |  | 9 |  |  | 24 |  |
| C10 |  | 10 |  |  | 25 |  |
| C11 |  |  | 11 |  |  | 26 |
| C12 |  |  | 12 |  |  | 27 |
| C13 |  |  | 13 |  |  | 28 |
| C14 |  |  | 14 |  |  | 29 |
| C15 |  |  | 15 |  |  | 30 |

This table shows an arrangement of 30 transducer elements (numbers 1 to 30 in the table) and shows which groups (G1 to G5) and which clusters (C1 to C15) they belong to. Sequential transducer element numbers represent neighboring elements.

By way of example, to transmit using transducer element 6, the bias circuit of group 2 is activated, and the transmit pulser circuits of cluster 6 is activated. The only transducer element which cannot be used for receive is element 21. The elements 7 to 10 may be used for reception.

The switching between receive and transmit is sufficiently fast that an element can be selected for transmission and then again for reception during the same firing.

Note that it is possible for each cluster to have only one transducer element, for example by having only the left half of the table above, for elements 1 to 15. However, preferably each cluster (i.e. second set) also to include multiple transducer elements. Furthermore, if there are receive and transmit circuitry for each element then transducer elements could instead be disabled via the receive and transmit circuitry.

There may be one or more elements used for receiving. For example elements 11 and 12 may be operated to receive the echo signals resulting from the transmission to element 6.

In general, the system for example comprises a number $N_1$ of transducer elements in each first set (i.e. how many elements in a group, where $N_1=5$ in this case), a number M of second sets (i.e. how many clusters there are, where M=15 in this case) and an aperture P which is the maximum distance (in number of elements) between the transmitting element and a receiving element.

It can be shown that:

$$P = N\text{clusters} - (N\text{elements}/N\text{groups}) + 1 = N\text{clusters} - \text{SizeGroup} + 1$$

Where Nclusters is the number of clusters, Nelements is the number of elements, Ngroups is the number of groups and SizeGroup is the number of elements per group.

From the table above it can easily be seen that this is the number of elements in a column, less one group of elements, and add 1.

For example, supposing element 10 is stimulated from the table above, then the element most far away for receive is element 20. The maximum distance (=P) is hence 11 (from 10 to 20 inclusive), Ngroup=6 and Nclusters=15.

The equation above is thus satisfied in this example as 11=15−30/6+1=15−5+1.

Thus, this relationship may be used to determine the number of clusters and the size of the groups to achieve a desired aperture.

By way of example the total number of transducer elements may be in the range 20 to 200.

Changing the bias voltage is a slow process and will generate acoustic energy. Thus, bias-voltage switching between transmit (TX) and receive (RX) modes is not possible. As a consequence, for any transducer element selected for transmission, only a set of the transducer elements (the ones with a bias voltage applied) is sensitive to receive ultrasonic energy.

The formation of sets does give some control limitations. For example, for the table above, element 10 in transmit mode can be combined with element 20 in receive mode as used in the example above but not with element 21 in receive mode as this would require that a bias voltage would be applied to group G2 and G5. This would cause malfunctioning as both element 6 and element 21 would be active in TX and RX mode unintentionally.

This limitation can be tolerated for a sideward facing annular system as described above, because the active aperture is always limited to a small portion of the circumference meaning that only a limited number of transducer element signals need to be collected to form the image.

The example above enables the number of transducer elements to be divided perfectly into the number of groups and clusters to form a full grid (and the number of clusters divides by the number of elements per group). This is not essential.

The table below shows how a 104 element array may be formed using 28 clusters and 13 groups. In this example the clusters (second sets) contain 3 or 4 elements (because the total number of elements does not divide exactly by the number of clusters).

The equation above in this example gives 21=28−104/13+1. For example, this may be from element 24 to 44 (inclusive).

TABLE 2

|  | G1 | G2 | G3 | G4 | G5 | G6 | G7 | G8 | G9 | G10 | G11 | G12 | G13 |
|---|---|---|---|---|---|---|---|---|---|---|---|---|---|
| C1 | 1 |  |  | 29 |  |  |  | 57 |  |  | 85 |  |  |
| C2 | 2 |  |  | 30 |  |  |  | 58 |  |  | 86 |  |  |
| C3 | 3 |  |  | 31 |  |  |  | 59 |  |  | 87 |  |  |
| C4 | 4 |  |  | 32 |  |  |  | 60 |  |  | 88 |  |  |
| C5 | 5 |  |  |  | 33 |  |  | 61 |  |  |  | 89 |  |
| C6 | 6 |  |  |  | 34 |  |  | 62 |  |  |  | 90 |  |
| C7 | 7 |  |  |  | 35 |  |  | 63 |  |  |  | 91 |  |
| C8 | 8 |  |  |  | 36 |  |  | 64 |  |  |  | 92 |  |
| C9 |  | 9 |  |  | 37 |  |  |  | 65 |  |  | 93 |  |
| C10 |  | 10 |  |  | 38 |  |  |  | 66 |  |  | 94 |  |
| C1 |  | 11 |  |  | 39 |  |  |  | 67 |  |  | 95 |  |
| C12 |  | 12 |  |  | 40 |  |  |  | 68 |  |  | 96 |  |
| C13 |  | 13 |  |  |  | 41 |  |  | 69 |  |  |  | 97 |
| C14 |  | 14 |  |  |  | 42 |  |  | 70 |  |  |  | 98 |

TABLE 2-continued

|     | G1 | G2 | G3 | G4 | G5 | G6 | G7 | G8 | G9 | G10 | G11 | G12 | G13 |
|-----|----|----|----|----|----|----|----|----|----|----|----|----|----|
| C15 |    | 15 |    |    | 43 |    |    | 71 |    |    |    |    | 99  |
| C16 |    | 16 |    |    | 44 |    |    | 72 |    |    |    |    | 100 |
| C17 |    |    | 17 |    | 45 |    |    |    |    | 73 |    |    | 101 |
| C18 |    |    | 18 |    | 46 |    |    |    |    | 74 |    |    | 102 |
| C19 |    |    | 19 |    | 47 |    |    |    |    | 75 |    |    | 103 |
| C20 |    |    | 20 |    | 48 |    |    |    |    | 76 |    |    | 104 |
| C21 |    |    | 21 |    |    | 49 |    |    |    | 77 |    |    |     |
| C22 |    |    | 22 |    |    | 50 |    |    |    | 78 |    |    |     |
| C23 |    |    | 23 |    |    | 51 |    |    |    | 79 |    |    |     |
| C24 |    |    | 24 |    |    | 52 |    |    |    | 80 |    |    |     |
| C25 |    |    |    | 25 |    | 53 |    |    |    |    | 81 |    |     |
| C26 |    |    |    | 26 |    | 54 |    |    |    |    | 82 |    |     |
| C27 |    |    |    | 27 |    | 56 |    |    |    |    | 83 |    |     |
| C28 |    |    |    | 28 |    | 56 |    |    |    |    | 84 |    |     |

Note that this example has a gap in the table between the last element and the first element which reduces the aperture size. It shows that the elements do not need to divide exactly into the segments. However it would be preferred for example to operate this design with 112 elements (14 groups) or slightly fewer, or with 84 elements (11 groups) or slightly fewer.

It will be immediately apparent that for a given number of elements, there are many ways to configure the groups and clusters, and this may be performed to achieve a desired aperture.

The signal processing a in IVUS system typically involves a synthetic aperture approach by which one element is stimulated at a time, and one (or more) surrounding elements are used to receiving at a time. Beamforming is carried out retrospectively by combining the signals of all combinations of transmission and reception elements.

As explained above, the invention is of particular interest for CMUT cells, where a bias voltage must be used to activate or deactivate the cells.

Figures 4, 5, 6:
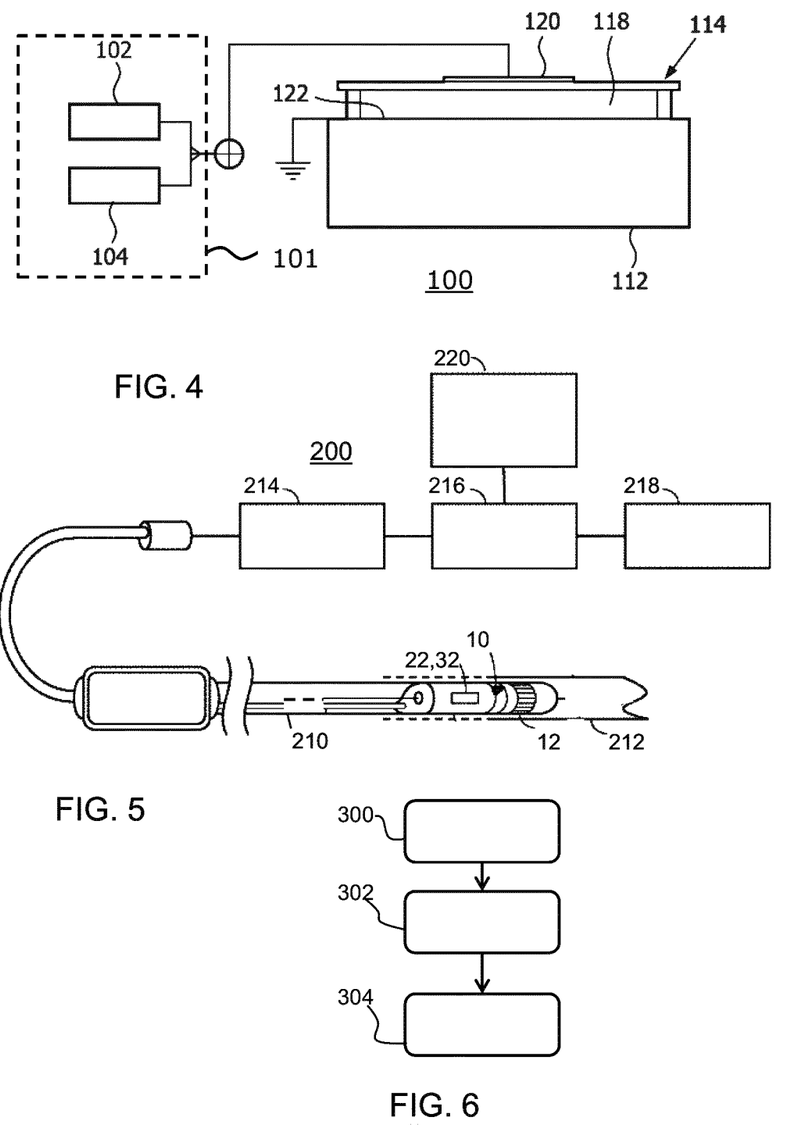
FIG. 4 shows a CMUT cell.
FIG. 5 shows an intravascular catheter based imaging system.
FIG. 6 shows an ultrasound imaging method.

For completeness, FIG. 4 shows a CMUT cell 100 having a flexible membrane or diaphragm 114 suspended above a silicon substrate 112 with a gap or cavity 118 there between. A first electrode 122 is located on the floor of the cell on the upper surface of the substrate 112 in this example. A second electrode 120 is located on the diaphragm 114 and moves with the diaphragm. In the example shown, the two electrodes are circular.

A dielectric (not shown) is provided on the substrate 112 and underneath the top (second) electrode 120. These two dielectrics may be equal in composition and thickness, but may be also asymmetric (different materials and thicknesses).

Other realizations of the electrode 120 design can be considered, such as electrode 120 may be embedded in the membrane 114 or it may be deposited on the membrane 114 as an additional layer. In this example, the first electrode 122 is circularly configured and embedded in the substrate layer 112 by way of non-limiting example. Other suitable arrangements, e.g. other electrode shapes and other locations of the first electrode 122, e.g. on the substrate layer 112 such that the first electrode 122 is directly exposed to the gap 118 or separated from the gap 118 by an electrically insulating layer or film to prevent a short-circuit between the second electrode 120 and the first electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 4 the first electrode 122 is grounded by way of non-limiting example. Other arrangements, e.g. a grounded second electrode 120 or both second electrode 120 and first electrode 122 floating are of course equally feasible.

The cell 100 and its gap 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell.

The electrodes of the CMUT cell 100 provide the capacitive plates of the device and the gap 118 is the dielectric between the plates of the capacitor. When the diaphragm vibrates, the changing dimension of the dielectric gap between the plates provides a changing capacitance which is sensed as the response of the CMUT cell 100 to a received acoustic echo. The cMUT is often used in collapsed mode; in that case, the dielectric gap looks like a donut shape with a varying width. Without a bias-voltage, the cMUT is not in collapse mode. The spacing between the electrodes is controlled by applying a static voltage, e.g. a DC bias voltage, to the electrodes with a voltage supply 101. The voltage supply 101 comprises separate stages 102, 104 for providing the DC and AC or stimulus components respectively of the drive voltage of the CMUT cells 100, e.g. in transmission mode. Indeed this invention makes use of this separation to enable the different stages to be allocated to different sets of transducer elements.

The first stage 102 may be adapted to generate the static (DC) voltage component and the second stage 104 may be adapted to generate an alternating variable voltage component or stimulus having a set alternating frequency, which signal typically is the difference between the overall drive voltage and the aforementioned static component thereof. The static or bias component of the applied drive voltage preferably meets or exceeds the threshold voltage for forcing the CMUT cells 100 into their collapsed states. This has the advantage that the first stage 102 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component.

Other suitable embodiments of the voltage source supply 101 should be apparent, such as for instance an embodiment in which the voltage source supply 101 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage source supply 101 may be implemented in any suitable manner.

It is known that by applying a static voltage above a certain threshold, the CMUT cell 100 is forced into a collapsed state in which the membrane 114 collapses onto the substrate 112. This threshold value may depend on the exact design of the CMUT cell 100 and is defined as the DC bias voltage, known as the collapse voltage, at which the membrane 114 sticks to (contacts) the cell floor through the force due to the electric field between the electrodes. The amount (area) of contact between the membrane 114 and the substrate 112 is dependent on the applied bias voltage. Increasing the contact area between the membrane 114 and the substrate 112 increases the resonant frequency of the membrane 114. Thus, the frequency response of a collapsed mode CMUT cell 100 may be varied by adjusting the DC bias voltage applied to the CMUT electrodes after collapse. As a result, the resonant frequency of the CMUT cell increases as a higher DC bias voltage is applied to the electrodes.

The invention makes use of a division of the AC and DC drive parts, as explained above. In addition, the cMUT bias voltage is applied to one node (e.g. the bottom electrode) and the stimulus voltage is applied to the other node (e.g. the top electrode).

FIG. 5 shows an intravascular catheter based imaging system 200, comprising the ultrasound imaging system 10 described above at the distal end of a catheter lumen 210 and inserted into a vessel 212. The catheter is coupled to a patient interface module 214, a computing system 216 and a monitor 218.

The computing system 216 receives the echo data from the imaging system by way of the patient interface module and processes the data to reconstruct an image of the tissue structures in the medium surrounding the imaging system. The echo data can used to generate a mixed-mode IVUS image including both B-scan and flow information. The B-scan image represents the two-dimensional anatomical structure of the tissue in a plane perpendicular to the longitudinal axis of IVUS devices, with brightness at any point of the image representing of the strength of the echo signal received from the corresponding location within the tissue. Flow data is associated with a visual representation of movement of elements in the medium surrounding the scanner such as blood flow. B-mode data (e.g., using the multi-frequency ultrasonic emissions) and flow data (e.g., using ultrasonic emission separated in time) can be collected, processed, and/or combined. The computing system 216 can also output a mixed mode image on the monitor. It can also be in communication with an angiographic/fluoroscopic imaging system 220.

FIG. 6 shows an ultrasound imaging method for performing imaging using the ultrasound system described above. The method comprises:

in step 300, operating a bias voltage circuit thereby to provide a bias voltage to a respective first set of transducer elements;

in step 302, operating a first transmit and receive circuit thereby to provide a transmit function to a first respective second set of transducer elements; and in step 304, operating a second transmit and receive circuit thereby to provide a receive function to a second respective second set of transducer elements, wherein the transducer elements of at least one first set differ from the transducer elements of at least one second set such that only a portion of transducer elements of the second set are arranged to be activated by its respective transmit and receive circuit upon application of a bias voltage to the at least one first set of the transducer elements by the respective bias voltage circuit. In a further embodiment of the method, the first set of the ultrasound transducers comprises a plurality of transducer elements, each one from a different second set, and each second set comprises at most one transducer element from any first set.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound system, comprising:
a plurality of transducer elements forming a one-dimensional (1D) array, wherein the 1D array is subdivided into a plurality of first subsets of the plurality of transducer elements, and wherein the 1D array is subdivided into a plurality of second subsets of the plurality of transducer elements;
a plurality of bias voltage circuits, each bias voltage circuit being in communication with a respective first subset of the plurality of first subsets and configured to apply a bias voltage to the transducer elements of its respective first subset; and
a plurality of transmit and receive circuits, each transmit and receive circuit being in communication with a respective second subset of the plurality of second subsets and configured to stimulate signal transmission or reception of the transducer elements of the respective second subset,
wherein each first subset differs from each second subset such that only a selected portion of each second subset is arranged to be activated by its respective one of the plurality of transmit and receive circuits upon application of a bias voltage to a selected first subset of the plurality of first subsets by its respective bias voltage circuit of the plurality of bias voltage circuits.

2. The ultrasound system as claimed in claim 1, wherein each first subset overlaps with each second subset such that each of the transducer elements in the same first subset is from a different second subset, and such that each second subset comprises at most one transducer element from any given first subset.

3. The ultrasound system as claimed in claim 1, wherein each second subset overlaps with each first subset such that each of the transducer elements from the same second subset is from a different first subset.

4. The ultrasound system as claimed in claim 1, wherein each first subset comprises a group of neighboring transducer elements.

5. The ultrasound system as claimed in claim 1, wherein each second subset comprises a cluster of non-neighboring transducer elements.

6. The ultrasound system as claimed in claim 5, wherein each second subset comprises a set of non-neighboring transducer elements spaced uniformly along the 1D array.

7. The ultrasound system as claimed in claim 1, wherein each transducer element comprises a plurality of CMUT cells.

8. The ultrasound system as claimed in claim 1, wherein the 1D array forms an annulus with each transducer element facing radially outwardly.

9. The ultrasound system as claimed in claim 1, characterized by the equation P=M−N1+1, wherein N1 is the number of transducer elements in each first subset, M is the number of second sets, P is the number of transducer elements that can be stimulated to receive simultaneously, which represents the maximum aperture size.

10. The ultrasound system as claimed in claim 1, further comprising an application specific integrated circuit (ASIC), wherein at least one of the plurality of bias voltage circuits and at least one of the plurality of transmit and receive circuits form a part of the ASIC.

11. An ultrasound imaging method for performing imaging using an ultrasound system comprising a plurality of transducer elements forming a one-dimensional (1D) array, a plurality of bias voltage circuits, and a plurality of transmit and receive circuits, wherein the 1D array is subdivided into a plurality of first subsets of the plurality of transducer elements, wherein the 1D array is subdivided into a plurality of second subsets of the plurality of transducer elements, and wherein each transducer element is adapted to be activated for transmission or reception by application of a bias voltage and connection to a respective transmit and receive circuit of the plurality of transmit and receive circuits,
wherein the method comprises:
operating a selected bias voltage circuit of the plurality of bias voltage circuits to provide a bias voltage to the transducer elements of a selected first subset of the plurality of first subsets,
operating a first transmit and receive circuit of the plurality of transmit and receive circuits to provide a transmit function to the transducer elements of a first respective second subset of the plurality of second subsets; and
operating a second transmit and receive circuit of the plurality of transmit and receive circuits to provide a receive function to the transducer elements of a second respective second subset of the plurality of second subsets,
wherein the each first subset differs from each second subset such that only a selected portion of each of the first and second respective second subsets is arranged to be activated by the first and second transmit and receive circuits respectively upon application of the bias voltage to the selected first subset by the selected bias voltage circuit.

12. The ultrasound imaging method as claimed in claim 11, wherein each first subset overlaps with each second subset such that each of the transducer elements in the same first subset is from a different second subset, and such that each second subset comprises at most one transducer element from any given first subset.

13. The ultrasound imaging method as claimed in claim 11, wherein each first subset comprises a group of neighboring transducer elements, and each second subset comprises a cluster of non-neighboring transducer elements.

14. The ultrasound imaging method as claimed in claim 11, wherein each second subset overlaps with each first subset such that each of the transducers from the same second subset is from a different first subset, wherein each first subset comprises a group of neighboring transducer elements and wherein each second subset comprises a cluster of non-neighboring transducer elements.

15. An intravascular ultrasound device, comprising;
a catheter body; and
an ultrasound system coupled to a distal portion of the catheter body, the ultrasound system comprising:
a plurality of transducer elements forming a one-dimensional (1D) array, wherein the 1D array is subdivided into a plurality of first subsets of the plurality of transducer elements, and wherein the 1D array is subdivided into a plurality of second subsets of the plurality of transducer elements;
a plurality of bias voltage circuits, each bias voltage circuit being in communication with a respective first subset of the plurality of first subsets and configured to apply a bias voltage to the transducer elements of its respective first subset; and
a plurality of transmit and receive circuits, each transmit and receive circuit being in communication with a respective second subset of the plurality of second subsets and configured to stimulate signal transmission or reception of the transducer elements of the respective second subset,
wherein each first subset differs from each second subset such that only a selected portion of each second subset is arranged to be activated by its respective one of the plurality of transmit and receive circuits upon application of a bias voltage to a selected first subset of the plurality of first subsets by its respective bias voltage circuit of the plurality of bias voltage circuits.

16. The intravascular ultrasound device as claimed in claim 15, wherein each first subset overlaps with each second subset such that each of the transducer elements in the same first subset is from a different second subset, and such that each second subset comprises at most one transducer element from any given first subset.

17. The intravascular ultrasound device as claimed in claim 15, wherein each second subset overlaps with each first subset such that each of the transducer elements from the same second subset is from a different first subset.

18. The intravascular ultrasound device as claimed in claim 15, wherein each first subset comprises a group of neighboring transducer elements.

19. The intravascular ultrasound device as claimed in claim 15, wherein each second subset comprises a cluster of non-neighboring transducer elements.

20. The intravascular ultrasound device as claimed in claim 19, wherein each second subset comprises a set of non-neighboring transducer elements spaced uniformly along the 1D array.

* * * * *